United States Patent [19]
Phillips

[11] Patent Number: 6,019,795
[45] Date of Patent: *Feb. 1, 2000

[54] CURVED PROSTHESIS

[76] Inventor: Van L. Phillips, P.O. Box 1873, Rancho Santa Fe, Calif. 92067

[ * ] Notice: This patent is subject to a terminal disclaimer.

[21] Appl. No.: 09/097,423

[22] Filed: Jun. 15, 1998

Related U.S. Application Data

[63] Continuation of application No. 08/485,003, Jun. 7, 1995, Pat. No. 5,766,265, which is a continuation of application No. 08/270,231, Jul. 1, 1994, Pat. No. 5,486,209, which is a continuation of application No. 07/977,654, Nov. 17, 1992, abandoned, which is a continuation of application No. 07/337,374, Apr. 13, 1989, Pat. No. 5,181,932, which is a continuation-in-part of application No. 07/029,947, Mar. 26, 1987, Pat. No. 4,822,363, which is a continuation-in-part of application No. 06/761,481, Aug. 1, 1985, abandoned.

[51] Int. Cl.$^7$ ........................................................ A61F 2/66
[52] U.S. Cl. ................................................. 623/55; 623/52
[58] Field of Search ................................... 623/52, 53, 55

[56] References Cited

U.S. PATENT DOCUMENTS

| | | |
|---|---|---|
| 25,238 | 8/1859 | Bly . |
| 61,780 | 2/1867 | Watson . |
| 277,562 | 5/1883 | Furrer . |
| 366,494 | 7/1887 | Marks . |
| 817,340 | 4/1906 | Rosenkranz . |
| 1,352,943 | 9/1920 | Dodge . |
| 1,424,264 | 8/1922 | Shrodes . |
| 2,075,583 | 3/1937 | Lange . |
| 2,379,538 | 7/1945 | Meierhofer . |
| 2,440,075 | 4/1948 | Campbell . |
| 4,461,103 | 7/1984 | Annovi . |
| 4,645,509 | 2/1987 | Poggi et al. ............................. 623/55 |
| 4,721,510 | 1/1988 | Cooper et al. .......................... 623/55 |
| 5,486,209 | 1/1996 | Phillips . |

FOREIGN PATENT DOCUMENTS

| | | |
|---|---|---|
| 1349393 | 12/1963 | France . |
| 2626463 | 2/1988 | France . |
| 3251711 | 9/1920 | Germany . |
| 776732 | 8/1977 | Russian Federation . |
| 0902746 | 2/1982 | U.S.S.R. . |
| 2139080 | 11/1984 | United Kingdom . |
| 2 139 089 | 11/1984 | United Kingdom . |

OTHER PUBLICATIONS

Burgess et al., "The Seattle Prosthetic Foot—A Design for Active Sports: Preliminary Studies", in Orthotics and Prosthetics (Michael J. Quigley, editor), pp. 25–31, 1983.

*Primary Examiner*—David H. Willse
*Attorney, Agent, or Firm*—Knobbe, Martens, Olson & Bear, LLP

[57] ABSTRACT

A prosthetic foot characterized by a forefoot portion having a heal portion damountably and interchangeably connected thereto. The forefoot portion and heel portion are fabricated from polymer impregnated and encapsulated laminates, including such laminates as carbon fibers and/or fiberglass or synthetic fibers such as Kevlar. The demountable connection of the heel portion permits interchangeability of heel and forefoot portions to match the weight, stride and activity schedule of the wearer utilizing the prosthetic foot. An auxiliary ankle member and wedge between the forefoot portion and the heel portion provide additional adjustability.

25 Claims, 2 Drawing Sheets

CURVED PROSTHESIS

RELATED APPLICATIONS

This application is a continuation of U.S. Ser. No. 08/485,003 filed Jun. 7, 1995, now U.S. Pat. No. 5,766,265, which is a continuation of U.S Ser. No. 08/270,231, filed Jul. 1, 1994, now U.S. Pat. No. 5,486,209, which is a continuation of U.S. Ser. No. 07/977,654, filed Nov. 17, 1992, abandoned, which is a continuation of U.S. Ser. No. 07/337,374, filed Apr. 13, 1989, now U.S. Pat. No. 5,181,932, which is a continuation-in-part of U.S. Ser. No. 07/029,947, filed Mar. 26, 1987, now U.S. Pat. No. 4,822,363, which is a continuation-in-part of U.S. Ser. No. 06/761,481, filed Aug. 1, 1985, abandoned.

BACKGROUND OF THE INVENTION

This invention relates to foot prostheses in general, and specifically to a prosthetic foot characterized by a unitary foot and heel construction, and/or an auxiliary ankle construction which permits the flexibility of the prosthesis to be selectively determined and easily changed. The invention also includes an improved coupling for attaching said foot prosthesis to an auxiliary pylon tube.

The prior art is replete with various types of mechanical devices purporting to solve the foot prosthesis problem. Typical of early devices is Lange 2,075,583, which incorporates a rubber form mounted in operative relationship with a rigid metallic core. Exemplary of the latest developments in the field is Poggi 4,645,509, which teaches a prosthetic foot incorporating a monolithic keel or beam of relatively massive proportions intended to react to the load of an amputee's body during walking, running, jumping, and the like and to release the resultant stored energy to create foot lift and thrust complementing the amputee's natural stride.

However, each of the prior art devices has significant deficiencies: specifically, the component parts of the prosthesis, as in Lange, are too heavy and too rigid or, as in Poggi, are too massive and monolithic to respond properly to the nuances of stress-response gradients characteristic of the human foot.

One of the primary factors which has inhibited the creation of a truly successful prosthetic foot has been the fixation of the prior art with the duplication of the structural aspects of the skeletal and muscular components of an actual human foot. In many instances, as exemplified by Poggi '509, mentioned hereinabove, even the toes of the foot are attempted to be duplicated by providing simulacra thereof. It is this fixation upon the mechanical elements of the human foot which has restricted the art to an attempt to duplicate the human foot components, a tendency which is particularly exemplified in Gajdos 3,335,428.

My copending application Ser. No. 07/293,824 discloses certain concepts relating to a prosthetic foot characterized by a forefoot portion and a heel portion which may be permanently or demountably associated with each other whereby both the forefoot portion and the heel portion can be readily exchanged with correspondingly constructed heel and forefoot portions. This exchangeability permits size adjustment or accommodation of different spring rates to suit the size of foot of the amputee or the stride and weight of the amputee, yielding an almost infinite range of combinations of spring rate and size to the amputee, and allowing a natural stride and resilience of gait which has not been obtainable by prior art prosthetic devices. Other than my present invention and my copending application, I am unaware of any prosthetic foot device incorporating such demountably attached forefoot and heel portions, and providing such ease and range of adjustability.

OBJECTS AND ADVANTAGES OF THE INVENTION

It is, therefore, an object of my invention to provide a foot prosthesis which is characterized by a forefoot portion and a heel portion which may be permanently or demountably associated with each other, with the forefoot portion having an upwardly extending attachment section providing ease of manufacture and resistance to rotation, whereby both the forefoot portion and the heel portion can be readily exchanged with correspondingly constructed forefoot and heel portions to provide size adjustment or accommodation of different spring rates to suit the size of foot of the amputee or the stride and weight of the amputee, and further adjustments can be made by the use of an auxiliary ankle spring member. Therefore, an almost infinite combination of spring rate and size can be provided to the amputee, achieving a natural stride and resilience of gait, which has not been obtainable by prior art prosthetic devices.

Another object of the invention is the provision in a prosthetic foot of the aforementioned character of an interchangeable or permanent forefoot portion which has a toe section, an arch section, a curvilinear ankle section, and an upwardly extending attachment section, all constructed without the necessity of tapering of the thickness thereof. Also incorporated in the aforementioned foot is an heel portion which has an attachment section secured to the intersection of the arch and toe sections of the forefoot portion and a heel section extending beyond the curvilinear ankle and attachment sections of the forefoot portion. The heel section extends beyond the curvilinear ankle and attachment sections of the forefoot portion.

As previously indicated, the forefoot portion can be provided in different sizes and spring rates, and an auxiliary ankle member may be utilized, thus permitting the gait, weight, and activity level of the amputee to be readily accommodated. Correspondingly, the forefoot portion can be demountably associated with the heel portion of the foot to permit different sizes of heel portion having different spring rates to be mounted in operative relationship with the forefoot portion.

Another object of the invention is the provision of a prosthetic foot of the aforementioned character in which both the forefoot and heel portions of the foot are fabricated, and the auxiliary ankle may be fabricated, from superimposed laminates maintained in operative relationship by an encapsulating polymer, and further in which said toe, arch, ankle and attachment sections of said forefoot portion, said heel section of said heel portion, and said auxiliary ankle attachment are susceptible to bending stress determined by the number of the laminates and polymers in the respective toe, arch, ankle and attachment sections of said forefoot portion, in said heel section of said heel portion, and in said auxiliary ankle attachment. Thus, the various portions and sections thereof are encapsulated in a polymer and capable of spring stress response as ankle loads are imposed thereupon during the utilization of said foot.

A further object of the invention is the provision, in a prosthetic foot of the aforementioned character, of a forefoot portion which consists of continuous, integrally and simultaneously formed toe, arch, ankle and attachment sections, said sections being fabricated as a unitary structure by polymer impregnation of superimposed reinforcing laminae maintained in the desired configuration of said forefoot portion and said toe, arch ankle and attachment sections being capable of spring stress generated energy storage whereby the subjection of the toe sections to bending moments will cause uniform transmission of spring stress through said arch section and through said curvilinear ankle section of said forefoot portion to said attachment section thereof.

Another object of the invention is the provision of the aforesaid prosthetic foot in which the curvilinear ankle section of said forefoot portion has its upper extremity constituted by said upper attachment section and its lower extremity extending into and constituting said arch section, said lower extremity, said curvilinear ankle section and said upper attachment section maintaining an approximately uniform thickness transversely of the longitudinal axis of said sections. Similarly, said heel portion and its various sections are provided with an approximately uniform thickness transversely of the longitudinal axis of said sections.

A further object of the invention is the provision of the aforesaid auxiliary ankle attachment, which is associated with the ankle section of said forefoot portion to increase the resistance of said ankle section to loads imposed upon the toe section of said forefoot portion. The concept of the auxiliary ankle involves the provision of ankle members characterized by different spring rates, which permits the resistance of the ankle section to deflection to be precisely adjusted to the weight, activity level and other characteristics of the individual for whom said foot is being adjusted.

The polymers utilized to encapsulate the fibrous laminae are characterized by elasticity and flexibility so that the forefoot and heel portions deflect proportionally to the engagement of said forefoot portion with an adjacent surface, causing the resultant energy to be stored and subsequently released when the gait of the amputee incorporating thrust and lift components results in the utilization of the stored energy and a consequent reduction of the energy expended by the amputee. There is a gradual increase in stiffness as the lever arm of the toe section of the forefoot portion shortens due to gradual deflection thereof.

It is an additional object of my invention to provide an improved coupling mechanism for attaching a prosthetic foot of the abovementioned character to an auxiliary pylon tube which is in turn attached to the wearer's leg.

In order to impart a cosmetic aspect to the prosthetic foot, after proper fitting of the foot to insure that the forefoot and heel portions and the auxiliary ankle are properly balanced and of appropriate size, the prosthesis may be encapsulated in a suitably shaped foot-like shroud to facilitate the utilization of the prosthetic foot with a conventional shoe. The enclosure must be sufficiently flexible so as not to inhibit the free movement and flexure of the forefoot and heel portions and the auxiliary ankle of the prosthetic foot, but, because of the inherently resilient and stress-absorbing characteristics of said foot, little dependence is needed upon the ancillary cushioning action of the enclosure.

Consequently, the foot of my invention is characterized by extreme light weight, instantaneous response to imposed loads and correspondingly instantaneous delivery of stored energy when the gait of the wearer indicates that such stored energy is to be released. Moreover, the foot may be readily mounted in operative relationship with conventional ancillary pylons and couplings, and can be finetuned by the blending of the forefoot and heel portions and auxiliary ankle characteristics to achieve the ultimate in operative response to the needs of the wearer.

Consequently, the wearer of the foot may engage in a wide variety of activities which were precluded in the past because of the structural limitations and corresponding performances of prior art prostheses. Running, jumping and other activities are sustained by the foot and it may be utilized in the same manner as the normal foot of the wearer.

Other objects and advantages of the invention will be apparent from the following specification and the accompanying drawings, which are for the purpose of illustration only.

DESCRIPTION OF PREFERRED EMBODIMENT

Figure 1:
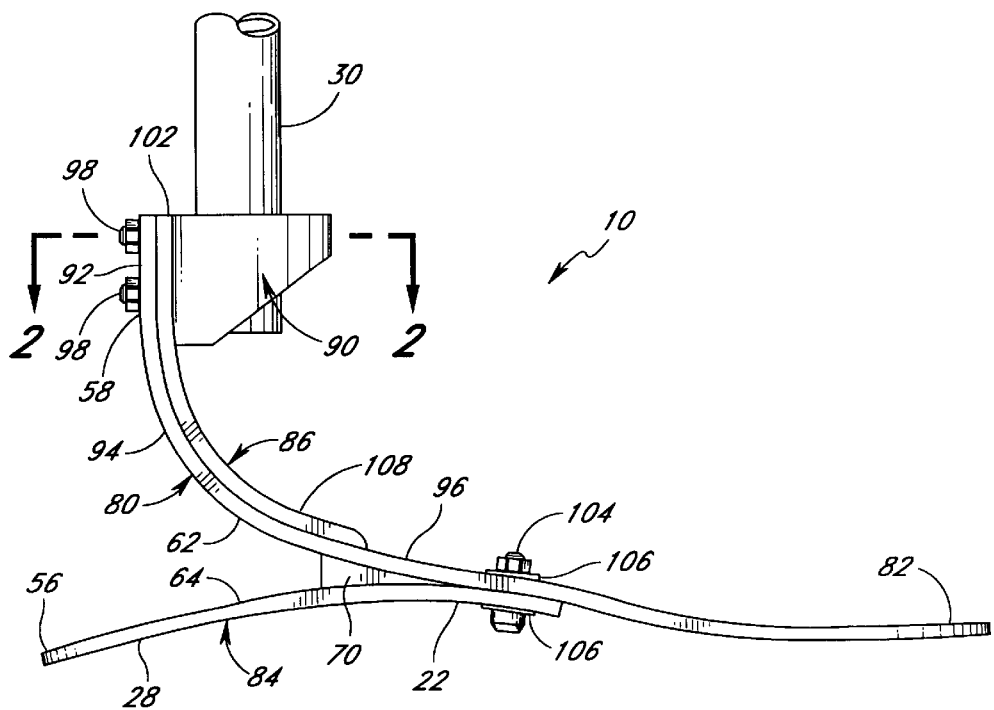
FIG. 1 is a side elevation view of portion of a prosthesis constructed in accordance with the teachings of the invention.
Figure 2:
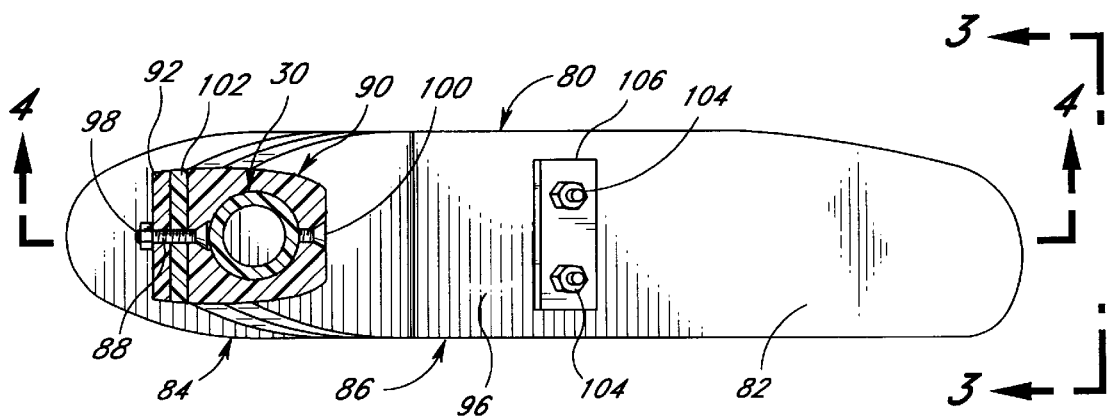
FIG. 2 is a partially sectional plan view, taken along line 2—2 of FIG. 1.
Figure 3:
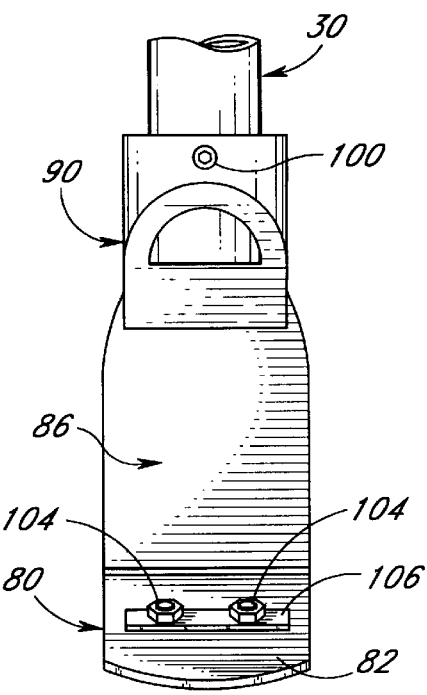
FIG. 3 is a front elevation view, taken along line 3—3 of FIG. 2.

Referring to the drawings, and particularly to FIGS. 1 and 2 thereof, I show a foot prosthesis 10 constructed in accordance with the teachings of the invention and including a forefoot portion 80 and a heel portion 84 operatively and demountably connected to each other by bolt and nut combinations 104 associated with load-transmitting metallic plates 106. If indicated, the forefoot and heel portions can be permanently secured to each other, as by epoxy adhesive or the like.

The forefoot portion 80 of the prosthesis 10 includes a substantially rigid upper attachment section 92, a curvilinear ankle section 94, an arch section 96 and a toe section 82. The sections 92, 94, 96 and 82 of the ankle portion 80 are formed integrally with one another and simultaneously by the incorporation of a plurality of laminae embedded in a hardened, flexible polymer.

Figure 4:
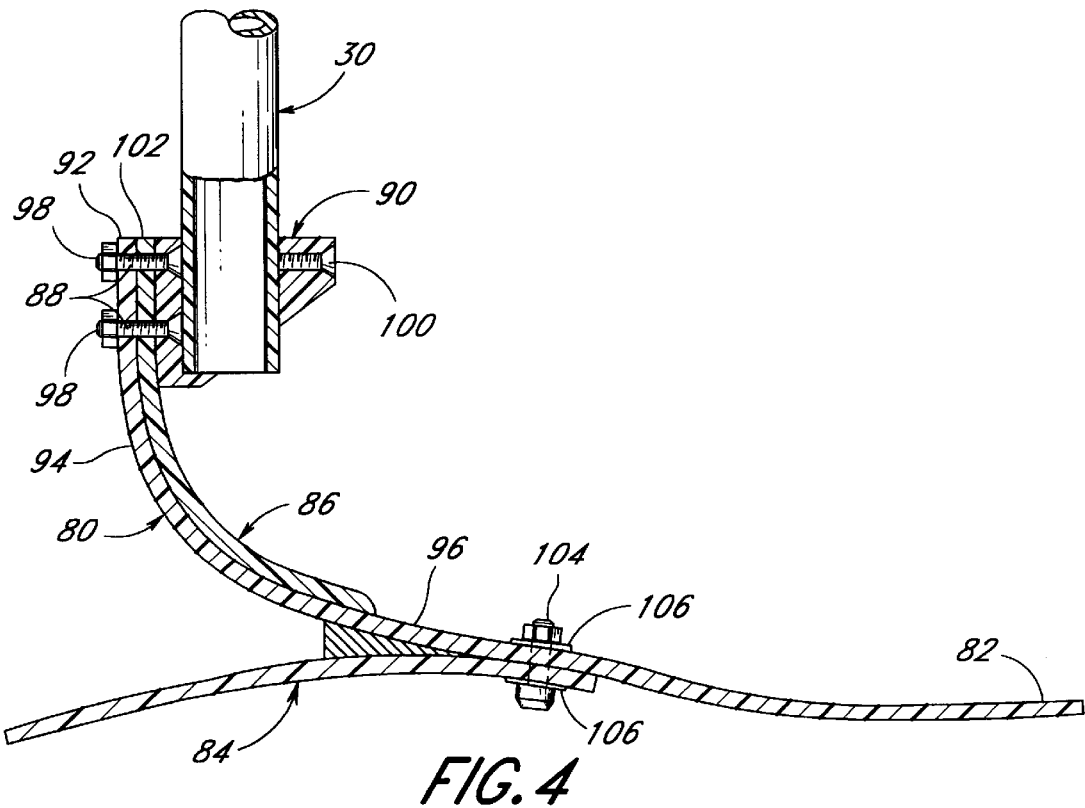
FIG. 4 is a partially sectional side elevation view, taken along line 4—4 of FIG. 2.

The attachment section 92 incorporates two centrally-located openings 88, FIG. 4. The attachment section 92 is substantially rigid and capable of sustaining torsional, impact and other loads impressed thereupon by the ankle portion 80 and heel portion 84 of the prosthesis. In addition, the inherent rigidity of the attachment section 92 causes the effective transmission of the aforesaid loads imposed thereupon to a suitable ancillary prosthetic pylon 30, by bolt and nut combinations 98 assembled through openings 88 to a pylon coupling 90. A screw 100 or other suitable attachment means secures the ancillary pylon 30 in the coupling 90.

In the particular embodiment of FIGS. 1–4, the auxiliary ankle 86 is mounted between the coupling 90 and ankle portion 80, and is secured in operative relationship with the ankle portion ankle section 94 through the use of centrally-located openings in an attachment section 102 of the ankle member 86, which openings are substantially aligned with openings 88 of the ankle portion attachment section 92. Bolt and nut combinations 98 retain the various components in the aforesaid operative relationship. Alternative embodiments would include securing the auxiliary ankle 86 to a rearward surface of the attachment section 92.

In the preferred embodiment, bolt and nut combinations 104, in conjunction with the load-distributing metallic plates 106, serve to secure the heel portion 84 in operative relationship with the forefoot portion 80 of the prosthesis. This mode of affixation facilitates the assembly or dismounting of selected heel portions 84 in operative relationship with selected forefoot portions 80, thus permitting a wide range of different sizes and stress load response characteristics to be related to each other to accomplish the optimum functional correspondence between the forefoot and heel portions 80 and 84.

An auxiliary ankle member 86 can be utilized to decrease the flexibility of the forefoot heel portion 80. The auxiliary ankle 86 is formed from fibrous laminates of the same character as the various portions of the prosthesis 10. In the preferred embodiment, the auxiliary ankle 86 incorporates an attachment section 102 which is operatively associated with the coupling 90 and the upper attachment section 92 of the forefoot portion 80, and preferably therebetween. The auxiliary ankle 86 is preferably secured in operative relationship with the curvilinear ankle section 94 of forefoot portion 80 through the aforementioned assembly of the coupling 90 with the bolt and nut combinations 98. On its end opposite from the attachment section 102, ankle member 86 has a tapered section 108 which provides a varying flexibility along the length of the ankle member 86 and also lessens the likelihood that the ankle member 86 will be undesirably snagged or restrained in its cooperative relationship with forefoot portion 80 and the cosmetic cover of the prosthesis, more thoroughly discussed below. In alternative embodiments, as will be understood by those skilled in the art, such tapering is not required in order to practice the invention, and accordingly, the ankle member 86 can be provided with a relatively uniform thickness along the length thereof.

In the preferred embodiment, the auxiliary ankle member 86 is secured against the relatively internal radius of the curvilinear ankle section 94, so that the anticipated upward deflection of a toe section 82 of the forefoot portion 80, as more thoroughly described below, will eventually cause deformation of the auxiliary ankle 86 as well as deformation of the ankle section 94, effectively combining the deformation resistance and energy storage characteristics of the auxiliary ankle member 86 with those of the ankle section 94. Alternative embodiments would include securing the auxiliary ankle 86 to the rearward surface of the attachment section 92 and further securing the auxiliary ankle tapered section 108 to an under surface 62 of the ankle section 94 in order to achieve the aforedescribed desired combination of the deformation resistance and energy storage characteristics of the auxiliary ankle member 86 with those of the ankle section 94.

The auxiliary ankle member 86 can be provided with different numbers of laminates to make it more or less compliant to loads transmitted through the ankle section 94. Consequently, when confronted with various anomalies in an amputee, such as overweight or excess activity levels, the basic structure of the forefoot portion 80, and more particularly the ankle section 94, can be materially modified to provide ankle portion action which is precisely adjusted to the needs of the amputee. Moreover, a variety of auxiliary ankle members 86 can be made available to an amputee, allowing the flexibility of the prosthesis to be adjusted on the basis of the particular activity which the amputee is undertaking.

As previously mentioned, a cosmetic cover, not shown, can be provided to shroud the prosthesis 10 after the optimum assemblage of the forefoot and heel portions 80 and 84 and any auxiliary ankle member 86 has been accomplished. Unlike prior art constructions, however, the cosmetic cover, which may be formed of low-density formed polymer, is not required to serve any ancillary shock-absorbing or other stress-isolating function since all of the loads imposed upon the prosthesis can be absorbed, transmitted and reasserted in a manner to be described in greater detail below.

The bolt and nut combinations 104, in conjunction with the load-distributing metallic plates 106, serve to secure the heel portion 84 in operative relationship with the forefoot portion 80 of the prosthesis 10, as best shown in FIGS. 1–2 of the drawings. The aforesaid mode of affixation facilitates the assembly or dismounting of selected heel portions 84 in operative relationship with selected forefoot portions 80 of the prosthesis 10, thus permitting a wide range of different sizes and stress load response characteristics to be related to each other to accomplish the optimum functional correspondence between the forefoot and heel portions 80 and 84 to accommodate to the maximum extent the needs of the wearer of the prosthesis, and, also, to provide for a proper mating of the prosthesis 10 with a selected, ancillary pylon 30 or the like.

The forefoot portion 80, as best shown in FIG. 1 of the drawings, includes a toe section 82, an arch section 96, a curvilinear ankle section 94, and an attachment section 92. The heel portion 84 includes an attachment section 22 and a heel section 28 which preferably has its rearward extremity 56 extending beyond an extreme rearward surface 58 of the forefoot portion attachment section 92 of the prosthesis 10. Mating bores, not shown, in the arch section 96 of the forefoot portion 80 and the heel portion 84 receive the respective bolt and nut combinations 104 to provide for the aforesaid facility in assembling and disassembling of the forefoot and heel portions 80 and 84. In the preferred embodiment, the various sections of the forefoot portion 80 are all constructed without the necessity of tapering of the thickness thereof, although those skilled in the art will understand that the invention is not limited to such nontapering construction.

Interposed between the under surface 62 of the ankle section 94 of the heel portion 84 and an upper surface 64 of the heel section 28 is a resilient, spring action function block 70 of wedge-shaped configuration to determine the lever arm of the heel section 28 and isolate the under surface 62 of the ankle section 94 and the upper surface 64 of the heel section 28 from each other. The function block 70 may be fabricated from a wide variety of resilient materials, including natural and synthetic rubbers or the like.

The materials from which the forefoot portion 80 and heel portion 84 and the auxiliary ankle 86 are fabricated must be such as to provide an energy-storing, resilient, spring-like effect. This is necessary because each engagement of the prosthesis 10 with an adjacent surface impresses compression, torsional and other loads upon the prosthesis 10 which must be stored within the prosthesis and then, dependent upon the stride of the wearer, be reimpressed upon said surface to achieve a natural stride conforming, ideally, in all respects to the stride of the unimpaired limb of the wearer of the prosthesis 10.

The forefoot and heel portions 80 and 84 and the auxiliary ankle 86 of the prosthesis are preferably molded as unitary components and are carefully formed to provide for uniform absorption of stress imposed thereupon. The configuration of both portions 80 and 84 is of utmost importance and the laminates and the polymer or polymers from which the portions 80 and 84 are fabricated must be resilient and capable of absorbing the compressive, torsional and other stresses referred to hereinabove and of restoring the stored energy created by such stresses, in a natural manner, to the impacted surface which originally imposed such stresses upon the prosthesis 10.

It has been found that there is a limited number of polymers capable of sustaining the significant stresses and repetitive loads imposed upon the prosthesis 10, particularly in the light of the countless numbers of cycles to which the prosthesis 10 is subjected during normal, everyday use.

At present, the best materials for the prosthesis are a composite of high-strength graphite fiber in a hightoughness epoxy thermosetting resin system. There are several reasons for this: (1) high strength; (2) stiffness to weight ratio of graphite as compared to other materials; (3) the almost complete return of input or stored energy; (4) light weight; (5) high fatigue strength; and (6) minimal creep. As an alternative material, fiberglass/epoxy is a fair choice, but it is not as good as graphite because of lower fatigue strength and higher density. Kevlar is even less acceptable due to poor compression and shear strength, although it is the lowest density of those mentioned.

An important aspect of the polymers and laminates referred to hereinabove is that they are characterized by needed, but not excessive, flexural deflection under load, which characteristic permits the shock-absorption stress loading of the prosthesis 10 while maintaining sufficient stability to prevent the collapse of the forefoot and heel portions 80 and 84 and the ankle member 86 of the prosthesis 10 while loads are imposed thereupon.

To achieve the relatively thin construction of the foot and ankle portions 80 and 84 and the auxiliary ankle member 86 of the prosthesis 10, the aforesaid polymers are utilized in conjunction with various laminating materials. Various types of fibrous laminae can be utilized to achieve the continuum required by the design of the foot and ankle portions 80 and 84 and the ankle member 86 to complement the stress-absorbing and storing characteristics of the polymers in which said fibrous laminae are embedded.

Of course, there is a wide variety of fibrous reinforcements in the form of laminae available at the present time, including such inorganic fibers as glass or carbon fibers. These inorganic fibers are customarily provided in tape or sheet form and can be readily superimposed in the sold to permit them to be encapsulated in the selected polymer.

Obviously, the number of superimposed laminae and the lengths thereof, together with the thickness of the encapsulating polymer, determine the stress characteristics of the resultant foot and ankle portions 80 and 84 and the ankle member 86 and, correspondingly, determine the total weight of the prosthesis 10. As will be apparent from the discussion hereinbelow, the individual foot and ankle portions 80 and 84 and ankle member 86 are designed to specifically accommodate individuals having different foot sizes, different weights and different strides and the individual design of the foot and ankle portions 80 and 84 and the ankle member 86 provides for matching, to an extent previously unknown in the art, the natural characteristics of the wearer's uninjured limb.

Furthermore, the function block 70 can be provided in different sizes and in materials having different compression characteristics so that the lever arm and the corresponding deflections of the heel section 28 may be increased or decreased.

As previously mentioned, the ankle section 94 is formed integrally with the upper attachment section 18 and said attachment section constitutes the upper extremity of the ankle section 94, while the initiation of the arch section 96 of the forefoot portion 80 constitutes the lower extremity of the ankle section 94. The configuration of the ankle section 94, in conjunction with the auxiliary ankle member 86, is the means whereby compressive loads imposed during impingement of the foot and ankle portions 80 and 84 upon an adjacent surface are absorbed and subsequently reimposed upon said surface. The ankle portion 94 and the auxiliary ankle member 86 are so designed that they function, substantially, as an ankle joint to permit pivoting of the forefoot portion 80 thereabout in a manner analogous to the manner in which the normal foot pivots about the normal ankle joint about an axis transversely of said ankle joint.

The radii of curvature of the ankle section 94 and any auxiliary ankle member 86 correspond to provide for the inherent resilience and deflection of the forefoot portion 80 while inhibiting undesired, excessive collapse of the ankle section 94.

It will be noted that the attachment section 22 of the heel portion 84 is substantially rigid and that the initial deflection of the heel section 28 occurs immediately adjacent the rearward extremity 56 of said heel section, terminating immediately adjacent the function block 70. Obviously, a greater length or less resilient function block 70 reduces the lever arm of the heel section 28 of the heel portion 84 and correspondingly reduces the modulus of deflection of said ankle section, while a smaller length or more resilient function block 70 increases the lever arm and correspondingly increases the deflection of the heel section 28 under load.

The toe section 82 and heel section 28 can be provided in different lengths to correspond to the size of the foot of the wearer of the prosthesis 10. When such different lengths are provided, corresponding reduction or increase in the number of laminae and thickness of taper of the respective toe section 82 and heel section 28 can be made to provide for the proper flexure of said toe and heel sections. It should also be noted that, even with the shortest heel section 28, the rearward extremity 56 thereof preferably projects beyond the rearward surface 58 of the forefoot portion 80. Consequently, the stabilizing and stress-absorption characteristics of the heel section 28 of the prosthesis 10 are always maintained.

Those skilled in the art will understand that many alternative embodiments of the coupling 90 can be constructed and practiced interchangeably in connection with the many alternative embodiments of the rest of the invention.

It will, of course, be obvious to those skilled in the art that, with respect to any embodiment of the invention, the fibrous reinforcements in the form of laminae plies encapsulated in the prosthesis may be fayed or tapered to accomplish a gradual transition as the number of plies is reduced in any area of the forefoot or heel portions.

Moreover, if a relatively lightweight individual partakes in sports or other activities which subject the prosthesis 10 to greater loads, a heel or forefoot portion 84 or 80 will be fitted which will accommodate for those greater loads.

The ankle section 94 of the forefoot portion 80 deflects under load and the auxiliary ankle member 86 similarly deflects. Additionally, the toe and arch sections 82 and 96 of the forefoot portion 80, and the heel section 28 of the heel portion 84, deflect under such load. Therefore, when subjected to vertical compression loads, the ankle section 94, the auxiliary ankle member 86, the arch section 96, and the toe and heel sections 82 and 28 absorb such loads.

Consequently, there is no stress concentration, either in the impact phase when the adjacent surface is initially contacted by the wearer of the prosthesis 10, or when return of the accumulated forces stored in the prosthesis 10 is accomplished.

The curvature of the toe section 82 provides for maximum accommodation of said section during surface contact in both the impact and delivery phases of the prosthesis 10. Similar considerations apply to the curvature of the heel section 28 of the heel portion 84 of the prosthesis 10. It will be noted that the curvatures of the toe and heel sections 82 and 28 provide for relatively extended lever arms which achieve stability and, also, stress storage and stress reaction.

The preferred method of manufacturing the forefoot and heel portions 80 and 84 and the auxiliary ankle member 86 of the prosthesis 10 is by a thermosetting molding process including the utilization of molds having properly shaped and sized cavities. The cavities are designed to receive the requisite number of laminates and the proper volume of polymer.

Unlike prior art unitary devices, the fitting of the prosthesis 10 involves the judicious adjustment of the prosthesis by the proper combination of forefoot and heel portions 80 and 84 and auxiliary ankle member 86, respectively. It also involves the selection of the properly designed ancillary pylon 30 which can be secured by means of the coupling 90 to the attachment section 92 of the forefoot portion 80. Only when the proper correlation between the forefoot portion 80, heel portion 84, auxiliary ankle member 86, and ancillary pylon 30 has been accomplished, can the cosmetic shroud, not shown, be installed upon the assembled, respective portions of the prosthesis 10.

By the prosthesis of my invention I provide a foot which can be carefully matched to the weight, stride and physical characteristics of the wearer. This is accomplished by carefully balancing the respective physical characteristics of the forefoot portion 80, the heel portion 84, the auxiliary ankle member 86, and the various sections thereof.

Moreover, the assembled prosthesis is far lighter in weight than prior art prostheses since the inherent design and structure of the prosthesis, the materials used and the careful calculation of stress factors of the components of the prosthesis permit fine-tung of the prosthesis to the needs of the wearer thereof.

It will be understood by those of skill in the art that the terms such as ankle, heel portion, arch and forefoot portion are used as convenient references to describe the geography of the prosthesis and are not intended to indicate that the prosthesis has a structural configuration replicating these regions of the human foot.

The prosthesis of my invention has been described with some particularity but the specific designs and constructions disclosed are not to be taken as delimiting of the invention in that various modifications will at once make themselves apparent to those of ordinary skill in the art, all of which will not depart from the essence of the invention and all such changes and modifications are intended to be encompassed within the appended claims.

I claim:

1. A prosthesis for supporting an amputee relative to a ground surface, comprising a main support member configured to support substantially the entire weight of said amputee, said main support member having a substantially flat forward surface and a substantially flat rearward surface, said main support member being elongated and having a cross-sectional shape that is substantially thinner in the fore and aft direction and substantially wider in the side-to-side direction such that it is capable of bending in the fore and aft direction and such that said main support member stores and releases walking energy during utilization of said prosthesis, said main support member having an upper end terminating in a substantially vertically oriented attachment section including a substantially flat vertically oriented attachment surface for attaching said prosthesis to a socket or other intermediate prosthesis and a lower end including a substantially curved generally horizontal section.

2. The prosthesis of claim 1 wherein said substantially curved generally horizontal section is sized and configured to provide rolling support relative to said ground surface.

3. The prosthesis of claim 1 wherein said main support member is monolothically formed from superimposed laminates maintained in operative relationship by an encapsulating polymer.

4. The prosthesis of claim 3 wherein said superimposed laminates taper from a relatively thick portion at said upper end to a relatively thin portion at said lower end providing desired bending characteristics along the length thereof.

5. A prosthesis for supporting an amputee relative to a ground surface, comprising a main support member and a heel member, said main support member having a substantially flat forward surface and a substantially flat rearward surface, said main support member being elongated and having a cross-sectional shape that is substantially thinner in the fore and aft direction and substantially wider in the side-to-side direction such that it is capable of bending in the fore and aft direction and such that said main support member stores and releases walking energy during utilization of said prosthesis, said main support member having an upper end terminating in a substantially vertically oriented attachment section including a substantially flat vertically oriented attachment surface for attaching said prosthesis to a socket or other intermediate prosthesis and a lower end including a substantially curved generally horizontal section, said heel member being connected to said lower end of said main support member.

6. The prosthesis of claim 5 further comprising an auxiliary support member attached at one end adjacent said upper attachment section of said main support member and extending downward and forward therefrom to reinforce said main support member so that said auxiliary support member and said main support member cooperate to determine the bending characteristics of said prosthesis.

7. The prosthesis of claim 6 wherein said auxiliary support member is tapered along its length to provide varied resistance to bending of said main support member.

8. A prosthesis for supporting an amputee relative to a ground surface, comprising:
   a first support member sized and configured to support substantially the entire weight of said amputee, said first support member having a cross-sectional shape that is substantially thinner in the fore and aft direction and substantially wider in the side-to-side direction such that it is capable of bending in the fore and aft direction and such that said first support member stores and releases walking energy during utilization of said prosthesis, said first support member having an upper end including an attachment section for attaching said prosthesis to a socket or other intermediate prosthesis, an intermediate ankle section and a lower end including a generally arcuate forward extending section; and
   a second support member configured to be selectively and removably secured to the lower end of said first support member and including a heel section extending rearward therefrom.

9. The prosthesis of claim 8 wherein said second support member further comprises a resilient member interposed between said heel section and said first support member for isolating said heel section from said first support member and to determine the lever arm of said heel section.

10. The prosthesis of claim 8 wherein said generally arcuate section is sized and configured to provide rolling support relative to said ground surface.

11. The prosthesis of claim 8 further comprising an auxiliary support member attached at one end adjacent said upper end of said first support member and extending downward and forward therefrom to reinforce the ankle section of said first support member so that said auxiliary support member and said first support member cooperate to determine the bending characteristics of said prosthesis.

12. The prosthesis of claim 11 wherein said auxiliary support member is tapered along its length to provide varied resistance to bending of said first support member.

13. The prosthesis of claim 8 wherein said first support member is monolothically formed from superimposed laminates in an encapsulating polymer.

14. The prosthesis of claim 13 wherein said superimposed laminates taper from a relatively thick portion at said upper end to a relatively thin portion at said lower end providing desired bending characteristics along the length thereof.

15. A prosthesis for supporting an amputee relative to a ground surface, comprising:
a primary support member sized and configured to support substantially the entire weight of said amputee, said primary support member comprising a monolithic composite material having a substantially rectangular cross-section that is thinner in the fore and aft direction and wider in the side-to-side direction such that it is capable of bending in the fore and aft direction and such that said primary support member stores and releases walking energy during utilization of said prosthesis, said primary support member having an upper end including an attachment section for attaching said prosthesis to a socket or other intermediate prosthesis, an intermediate ankle section curving downward and forward from said upper end and a lower end including a forward extending toe section; and
an elongated secondary support member attached at one end adjacent said upper end of said primary support member and extending downward and forward therefrom to reinforce said ankle section so that said secondary support member and said primary support member cooperate to determine the overall bending characteristics of said prosthesis, said secondary support member configured to store energy primarily by bending.

16. The prosthesis of claim 15 further comprising heel member secured to the lower end of said primary support member and extending rearward therefrom.

17. The prosthesis of claim 16 further comprising a resilient member interposed between said heel member and said primary support member for isolating said members from one another and to determine the lever arm of said heel member.

18. The prosthesis of claim 15 wherein said forward extending toe section is generally curved so as to provide rolling support relative to said ground surface.

19. The prosthesis of claim 15 wherein said secondary support member is tapered along its length to provide varied resistance to bending of said primary support member.

20. The prosthesis of claim 15 wherein said primary support member is monolothically formed from superimposed laminates maintained in operative relationship by an encapsulating polymer.

21. The prosthesis of claim 20 wherein said superimposed laminates taper from a relatively thick portion at said upper end to a relatively thin portion at said lower end providing desired bending characteristics along the length thereof.

22. A prosthesis for supporting an amputee relative to a ground surface, comprising:
a first support member sized and configured to support substantially the entire weight of said amputee, said first support member having a cross-sectional shape that is substantially thinner in the fore and aft direction and substantially wider in the side-to-side direction such that it is capable of bending in the fore and aft direction and such that said first support member stores and releases walking energy during utilization of said prosthesis, said first support member having an upper end including an attachment section for attaching said prosthesis to a socket or other intermediate prosthesis, an intermediate ankle section and a lower end including a generally arcuate forward extending section;
a second support member secured to the lower end of said first support member and including a heel section extending rearward therefrom; and
an auxiliary support member attached at one end adjacent said upper end of said first support member and extending downward and forward therefrom to reinforce the ankle section of said first support member so that said auxiliary support member and said first support member cooperate to determine the bending characteristics of said prosthesis.

23. The prosthesis of claim 22 wherein said auxiliary support member is tapered along its length to provide varied resistance to bending of said first support member.

24. A prosthesis for supporting an amputee relative to a ground surface, comprising:
a primary support member sized and configured to support substantially the entire weight of s aid amputee, said primary support member comprising a monolithic composite material having a substantially rectangular cross-section that is thinner in the fore and aft direction and wider in the side-to-side direction such that it is capable of bending in the fore and aft direction and such that said primary support member stores and releases walking energy during utilization of said prosthesis, said primary support member having an upper end including an attachment section for attaching said prosthesis to a socket or other intermediate prosthesis, an intermediate ankle section curving downward and forward from said upper end and a lower end including a forward extending toe section;
a secondary support member attached at one end adjacent said upper end of said primary support member and extending downward and forward therefrom to reinforce said ankle section so that said secondary support member and said primary support member cooperate to determine the overall bending characteristics of said prosthesis; and
a heel member secured to the lower end of said primary support member and extending rearward therefrom.

25. The prosthesis of claim 24 further comprising a resilient member interposed between said heel member and said primary support member for isolating said members from one another and to determine the lever arm of said heel member.

\* \* \* \* \*